United States Patent
Grimm et al.

[11] Patent Number: 5,649,958
[45] Date of Patent: Jul. 22, 1997

[54] INSTRUMENT FOR SURGICAL PURPOSES

[75] Inventors: Holger Grimm, Deisslingen; Klaus Hebestreit; Pedro Morales, both of Tuttlingen, all of Germany

[73] Assignee: Aesculap AG, Tuttlingen, Germany

[21] Appl. No.: 649,687

[22] PCT Filed: Oct. 15, 1994

[86] PCT No.: PCT/EP94/03400

§ 371 Date: May 31, 1996

§ 102(e) Date: May 31, 1996

[87] PCT Pub. No.: WO95/15722

PCT Pub. Date: Jun. 15, 1995

[30] Foreign Application Priority Data

Dec. 8, 1993 [DE] Germany ............. 43 41 734.5

[51] Int. Cl.$^6$ ................................................. A61B 17/28
[52] U.S. Cl. ................................... 606/208; 606/206
[58] Field of Search ........................... 606/208, 170, 606/205, 167, 206, 174

[56] References Cited

U.S. PATENT DOCUMENTS

| | | |
|---|---|---|
| 4,369,788 | 1/1983 | Goald . |
| 4,712,545 | 12/1987 | Honkanen . |
| 5,507,774 | 4/1996 | Holmes et al. ............... 606/208 |
| 5,522,830 | 6/1996 | Aranyi ........................ 606/208 |

FOREIGN PATENT DOCUMENTS

| | | |
|---|---|---|
| 92 02 132.8 | 6/1992 | Germany . |
| 93 07 622.3 | 9/1993 | Germany . |

*Primary Examiner*—Michael Buiz
*Assistant Examiner*—Kevin Truong
*Attorney, Agent, or Firm*—Barry R. Lipsitz

[57] ABSTRACT

An instrument for surgical purposes has two relatively movable working parts and two relatively pivotable jaws interconnected in such a way that when they are opened, the two working parts are pushed together, whereby one of the two jaws has a shaft for the pivotable fitting of the other. The shaft is provided with regions of differing diameter and can be axially moved in such a way that selectively a larger or smaller-diameter region is effective in the region of the other jaw, which has a slot for the shaft with a narrower central section and broadened bearing sections at both ends. The width of the slot in the narrower central section lies between the diameter of the two regions of the shaft and has a diameter in the circularly broadened bearing sections corresponding to the larger diameter of the shaft. One of the two jaws articulatingly engages one working part with a catch when the shaft transfixes the broadened bearing section, but releases the working part when the shaft transfixes the other bearing section.

10 Claims, 4 Drawing Sheets

5,649,958

INSTRUMENT FOR SURGICAL PURPOSES

BACKGROUND OF THE INVENTION

The invention relates to an instrument for surgical purposes comprising two working parts displaceable relative to each other and two handle branches pivotable relative to each other, one of the handle branches being connected to the one working part and the other to the other working part such that when closing and opening the handle branches, the two working parts are displaced relative to each other, and one of the two handle branches carrying for pivotable mounting of the other handle branch a bearing shaft, which has regions of different diameter and is axially displaceable such that in the region of the other handle branch a region of larger or a region of smaller diameter is selectively effective, and the other handle branch having a slot for the bearing shaft with a narrower central section and a widened bearing section at one end, the width thereof in the narrower central section lying between the diameter of the two regions of the bearing shaft and having in the circular, widened bearing section a diameter which corresponds to the larger diameter of the bearing shaft, and one of the two handle branches entering articulatedly with a driver into engagement with the one working part when the bearing shaft extends through the widened bearing section.

Instruments of this kind are widely used in the surgical sector, for example, in the form of so-called tubular shaft instruments or biopsy forceps, etc. In order to dismantle these instruments for cleaning purposes and to exchange parts, it is necessary to release the connection between the working parts, on the one hand, and the handle branches, on the other hand. In particular, with very small instruments this is partly rather complicated, as reliable connections are necessary for the transmission of the high forces and are not easily released.

Such instruments are known wherein the operative connection between a handle branch and a displaceable working part is released by the handle branch being designed so as to be longitudinally displaceable in its bearing on the other handle branch so that with the longitudinal displacement, the engagement with the working part is released (DE-U-93 07 622). However, the design thereof is chosen such that upon release of the operative connection between a handle branch and a moved working part, the handle branches are automatically completely released from one another, i.e., the entire instrument is disassembled.

The object of the invention is to further develop a generic instrument such that release of the operative connection between handle branch and working part is possible without complete disassembly of the instrument in the region of the handle branches being necessary.

SUMMARY OF THE INVENTION

This object is accomplished in accordance with the invention in an instrument of the kind described at the outset in that there is arranged at the other end of the central section another widened bearing section with a likewise widened diameter, and in that the driver disengages the working part when the bearing shaft extends through this other widened bearing section.

Two bearing positions are thus provided in which the handle branches are articulatedly connected to each other, and between these two bearing positions the two handle branches can be displaced relative to each other, with engagement with the working part occurring in one bearing position, and not in the other bearing position. With this construction, it is ensured that the handle branches always remain articulatedly connected to each other, also when the operative connection with the working part is released.

It is advantageous for the shaft to be displaced under spring load into a position in which the region of larger diameter is effective at the handle branch mounted on the shaft. It is thereby ensured that the shaft is normally pushed into one of the two end bearing positions so that the handle branches are mounted on each other in a properly guided way. For displacement between the two positions and passage through the narrower central section, the shaft has to be displaced against the spring load.

In a preferred embodiment, provision is made for the shaft to have a head made of elastically deformable material which is supported on the outer side of a handle branch and is elastically deformable over the entire axial path of displacement of the shaft while being permanently supported on the handle branch. This makes it possible to dispense with separate spring elements. In this embodiment, there is, for example, no longer any necessity for helical springs as the resetting spring load is brought about by the elastic deformation of the head.

In particular, it is expedient for the head in the undeformed state to have the shape of an approximately spherical half shell which is supported with its edge on the handle branch and in its central part is connected to the shaft. In this way, a relatively large displacement path is possible without the head requiring very large dimensions at the sides.

In a further preferred embodiment, provision is made for the shaft to include a stepped metal sleeve in which a shaft connected to the head is inserted. In particular, from the opposite side of the shaft, a counterpart which is connected to the shaft and covers the end face of the metal sleeve can be inserted into the latter. Herein, it is particularly advantageous for a connection between shaft and counterpart to be a detent connection.

In a preferred embodiment which is preferably employed for tubular shaft instruments, provision is made for the moved working part to have a spherical end which is connected to the working part via a web of smaller dimensions.

Herein, provision may be made for the driver to be a blind hole bore in the handle branch which extends essentially parallel to the slot and is open via a lateral longitudinal slot, the width of which is smaller than the diameter of the spherical end and larger than the width of the web.

The slot is preferably arranged essentially perpendicular to the direction of displacement of the working part.

BRIEF DESCRIPTION OF THE DRAWINGS

The following description of preferred embodiments serves in conjunction with the drawings to explain the invention in further detail. The drawings show:

FIG. 4 a sectional view along line 4—4 in FIG. 3 with the shaft not pushed in.

DESCRIPTION OF THE PRESENT INVENTION

Figure 1:
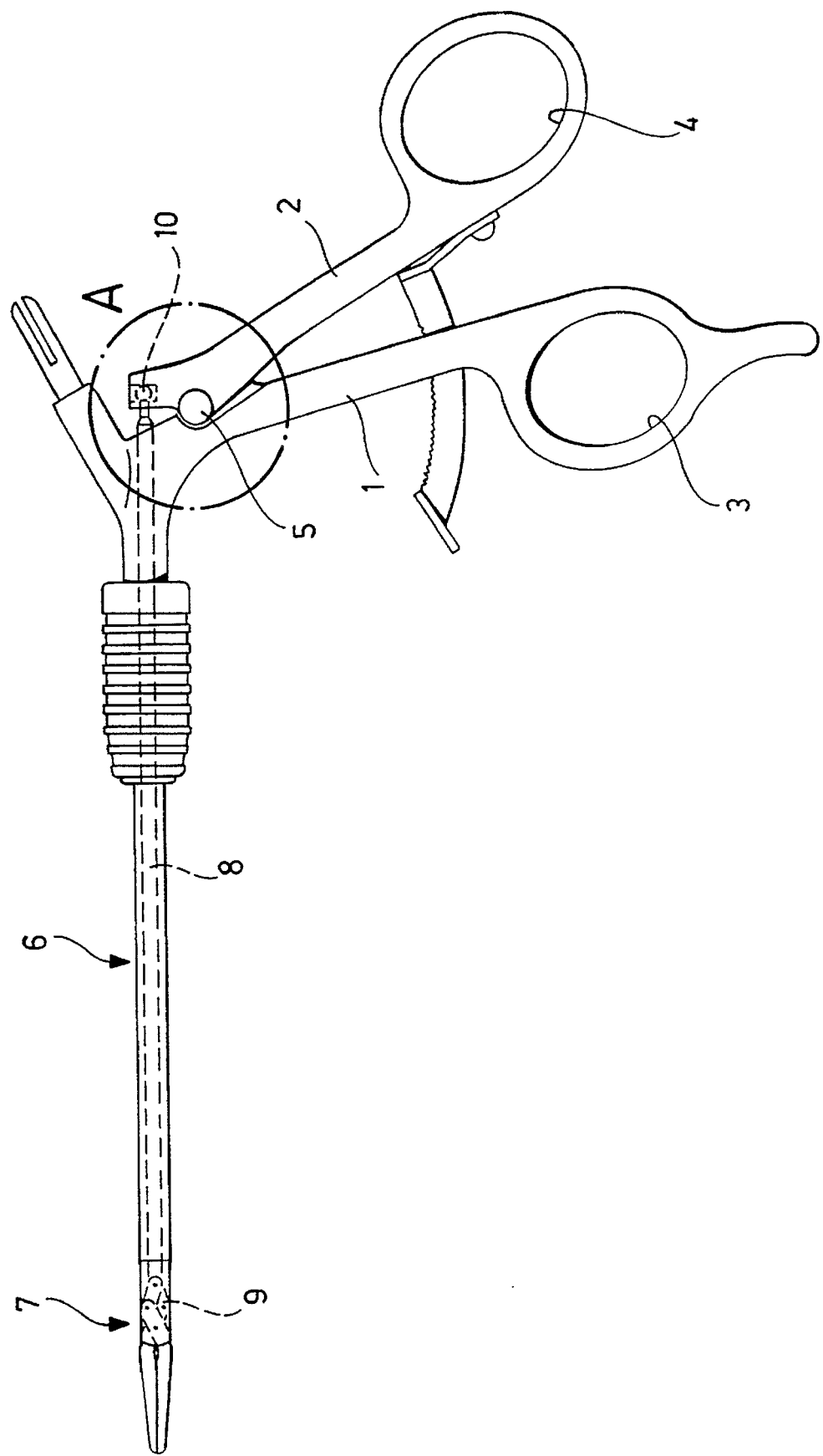
FIG. 1 a side view of a tubular shaft instrument.

The tubular shaft instrument illustrated in the drawings comprises two handle branches 1 and 2 with finger openings 3 and 4, respectively, which are connected to one another for pivotal movement about a bearing point 5. One of the two handle branches 1 carries a tubular shaft 6 with a tool 7 held on the free end thereof. This tool 7 is articulatedly connected to a rod-shaped working part 8 which is arranged for longitudinal displacement in the shaft 6 and protrudes from the latter at the rear side thereof. There, the working part 8 is articulatedly connected to the other handle branch 2 so that it is pushed back and forth in the shaft 6 when the handle branches 1 and 2 are opened and closed. The working part 8 thereby actuates the tool 7 via gear parts 9. This tool 7 can have a cutting function or it can be forceps. Other tools are also possible.

The articulated connection between the end of the working part 8 protruding from the shaft 6, on the one hand, and the handle branch 2, on the other hand, is effected via a spherical end 10 on the working part 8, which is connected via a web 11 to the working part 8. This web 11 has smaller transverse dimensions than the spherical end 10, i.e., in the region of the web 11 the working part 8 is constricted and reduced in relation to its other external circumference.

The handle branch 2 contains a blind hole bore 12 with a lateral opening 13 having the shape of a longitudinal slot. The blind hole bore 12 receives the spherical end 10 of the working part 8, the slot-shaped opening 13 the web 11. The opening 13 is less wide than the spherical end 10 of the working part 8 and so the spherical end 10 encompassed in the blind hole bore 12 is taken along when the handle branch 2 is pivoted. The internal diameter of the blind hole bore 12 preferably corresponds to the diameter of the spherical end 10 and so press movements are also directly transferred onto the working part 8.

In the region of the bearing point 5, the handle branch 2, which in the region of the bearing point is of two-layered construction and receives the handle branch 1 between it, carries two openings 14 and 15 in alignment with each other and a bearing shaft 16. The latter is formed by a metal sleeve 17 which widens in stepped configuration, and into one side of which a head part 19 provided with a shaft 18 is inserted. Inserted in the metal sleeve 17 from the other side is a counterpart 20 which covers the end face of the metal sleeve 17 and is connected to the shaft 18 by a detent connection, not illustrated separately in the drawings. The head part 19 has a head 21 in the form of a spherical half shell, which is supported with its edge 22 on the outer side of the handle branch 2 and is connected in its central region to the shaft 18. The head part 19 consists of an elastically deformable material, preferably an elastomeric plastic. The counterpart 20 can also consist of plastic.

Figure 4:
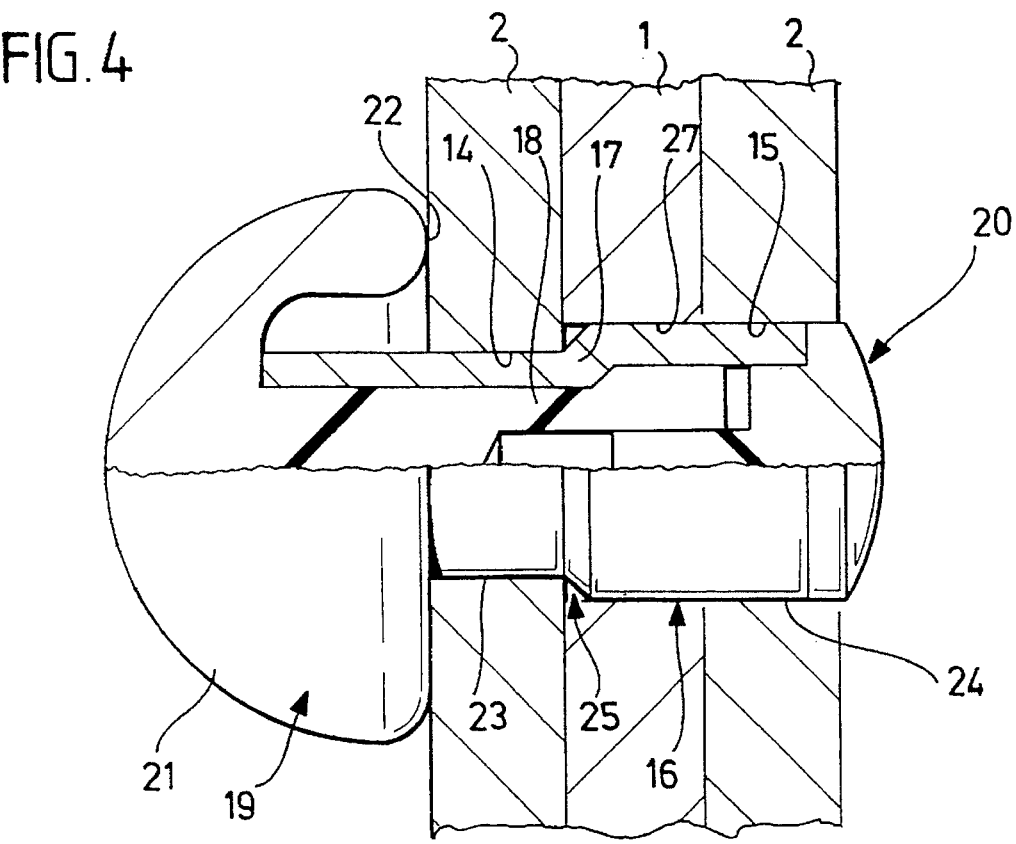
Figure 5:
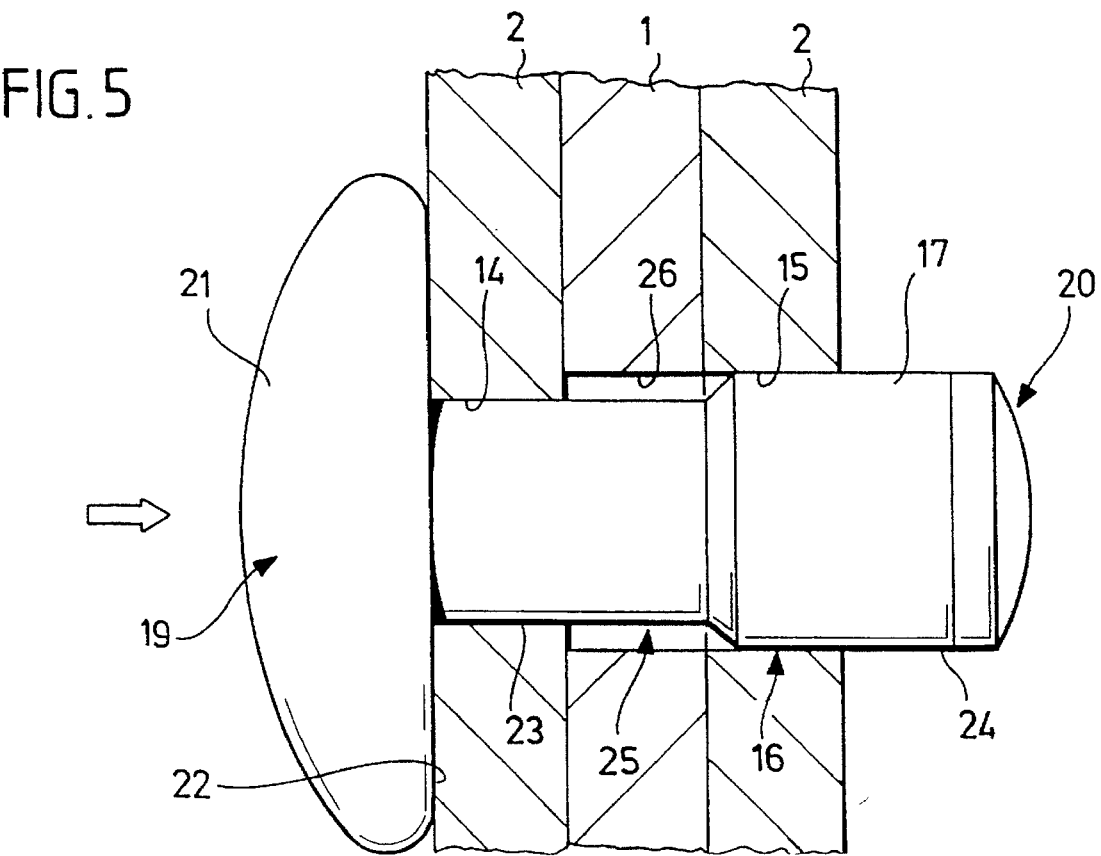
FIG. 5 a view similar to FIG. 4 with the shaft pushed in in the direction of the arrow.

The opening 14 of the handle branch 2 close to the head 21 is adapted in its dimensions to a region 23 of the metal sleeve 17 with a smaller external diameter, the more remote opening 15 of the handle branch 2 to a region 24 with a larger diameter. By pressing on the head 21, the bearing shaft 16 is pushable so far into the openings 14 and 15 that the region 23 of smaller diameter reaches into the opening 15 of the handle branch 2, i.e., extends through the entire thickness of the handle branch 1, as is illustrated in FIG. 5. The head 21 thereby becomes strongly deformed under the effect of the pressure on the bearing shaft 16. Therefore, when released, owing to its elastic properties, the head 21 pulls the bearing shaft 16 back into the initial position illustrated in FIG. 4, and the head 21 assumes its original shape again. In this way, a recovery spring force is obtained without any separate spring elements being required therefor.

In the region of the bearing point 5, the handle branch 1 has an opening 25 which extends in the longitudinal direction of the handle branch and has a central section 26 of smaller width and at each of both ends thereof a circular bearing section 27, 28 of larger diameter. In its entirety, a double keyhole shape is thus imparted to this opening 25. The width of the central section 26 is adapted to the diameter of the region 23 of the bearing shaft, the diameter of the bearing sections 27 and 28 to the region 24 of larger diameter.

Figure 2:
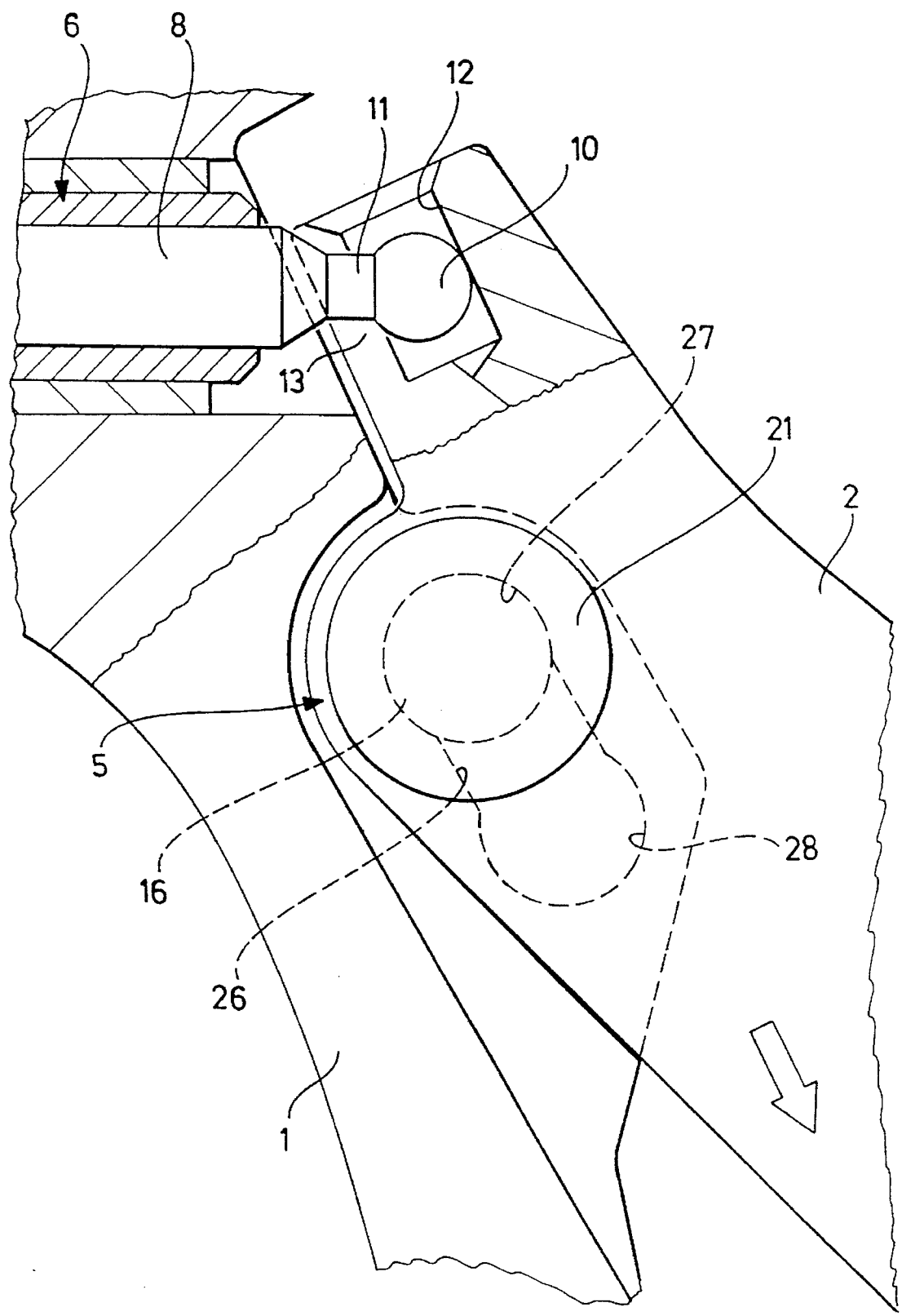
FIG. 2 an enlarged, partly broken-open illustration of section A in FIG. 1 with the handle branch in engagement with the working part.
Figure 3:
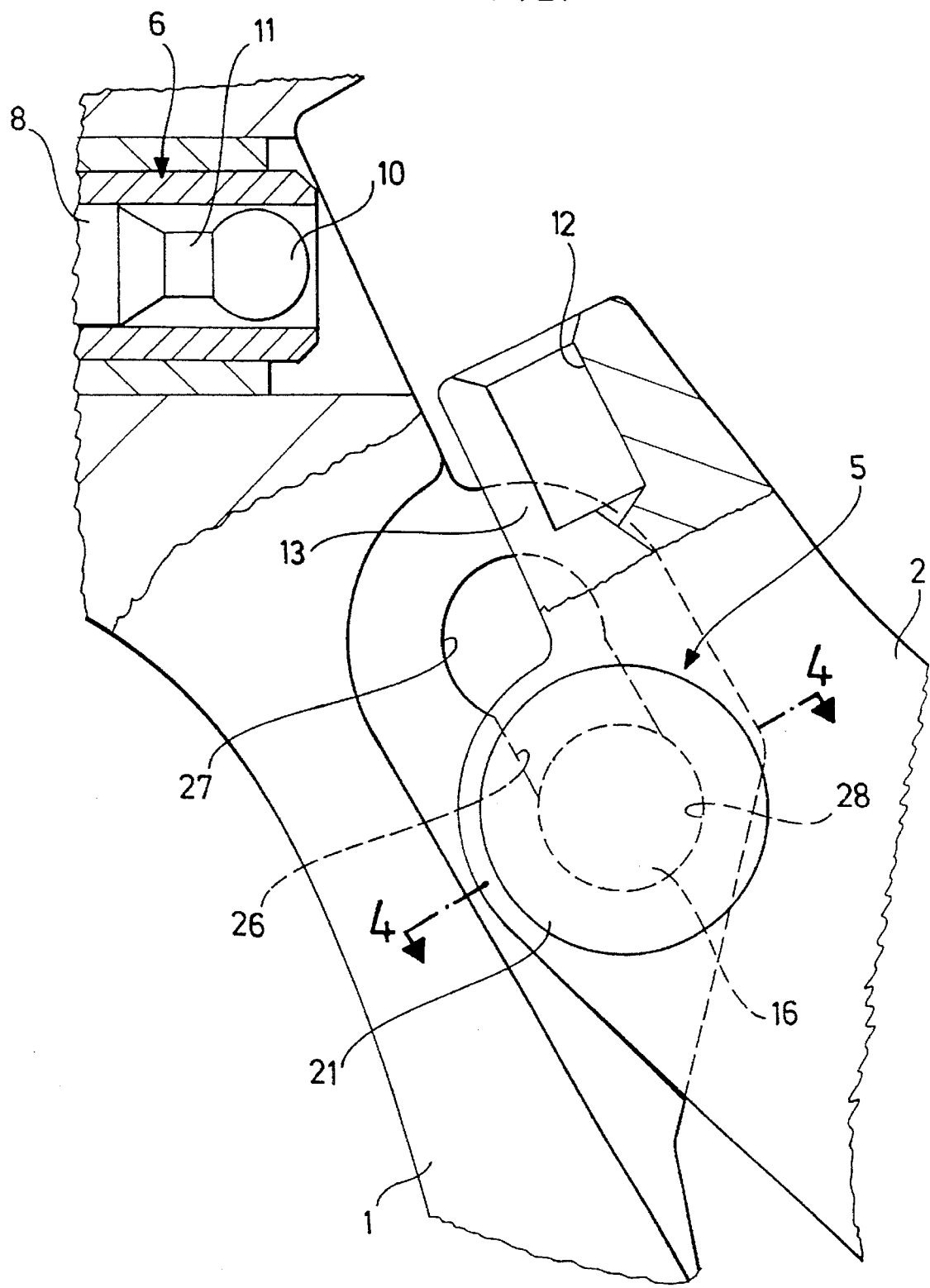
FIG. 3 a view similar to FIG. 2 with the handle branch released from the working part.

In the normal bearing state, illustrated in FIG. 2, the bearing shaft 16 passes through the bearing section 27 of the handle branch 1. Owing to the elastic recovery force of the head 21, the bearing shaft 16 is positioned such that its region 24 extends into the bearing section 27, and the handle branch 1 is thus mounted on the handle branch 2 for pivotal movement about a fixed axis of rotation. The latter is arranged such that in this bearing position, the spherical end 10 of the working part 8 extends into the blind hole bore 12 of the handle branch 2 (FIG. 2).

When the bearing shaft 16 is displaced into the pushed-in position illustrated in FIG. 5, the region 23 of smaller diameter enters the opening 25, and the handle branch 1 can then be displaced in the longitudinal direction relative to the handle branch 2 until the bearing shaft 16 enters the opposite bearing section 28 of the opening 25. During this displacement, the spherical end 10 of the working part 8 emerges upwardly from the blind hole bore 12 and so the operative connection between handle branch 2 and working part 8 is disengaged. After the bearing shaft 16 enters the bearing section 28, the bearing shaft 16 can be moved back again into its initial position by releasing the head 21. Owing to the elastic properties of the head 21, the region 24 of larger diameter is thereby pushed into the bearing section 28 and so both handle branches are now pivotable with one another again about a defined axis, but the latter is laterally offset in relation to the original bearing axis.

In the same way, the displacement can take place in the reverse direction, with the spherical end 10 of the working part 8 then being introducible into the blind hole bore 12 again so that an operative connection is again established between the handle branch 2 and the working part 8.

We claim:

1. An instrument for surgical purposes comprising:
   two working parts displaceable relative to each other and two handle branches pivotable relative to each other,
   one of said handle branches being connected to one of said working parts and the other of said handle branches being connected to the other working part such that when closing and opening said handle branches, said two working parts are displaced relative to each other,
   one of said two handle branches carrying a bearing shaft for pivotable mounting of said other handle branch, said bearing shaft having regions of different diameter and being axially displaceable such that in the region of the other handle branch one of a larger diameter region and a smaller diameter region is selectively effective,
   said other handle branch having a slot for said bearing shaft with a narrower central section and a circular, widened bearing section at one end, the width thereof in the narrower central section lying between the diameter of said two regions of said bearing shaft and having in said circular, widened bearing section a diameter which corresponds to the larger diameter region of said bearing shaft,
   one of said two handle branches entering articulatedly with a driver into engagement with said one working part when said bearing shaft extends through said widened bearing section, wherein there is arranged at the other end of said central section another widened bearing section with a likewise widened diameter, and said driver disengages said working part when said bearing shaft extends through this other widened bearing section.

2. Instrument as defined in claim 1, wherein said bearing shaft is displaced under spring load into a position in which said region of larger diameter is effective at said handle branch mounted on said bearing shaft.

3. Instrument as defined in claim 2, wherein said bearing shaft has a head made of elastically deformable material which is supported on the outer side of a handle branch and is elastically deformable over the entire axial path of displacement of said bearing shaft while being permanently supported on said handle branch.

4. Instrument as defined in claim 3, wherein in the undeformed state, said head has the shape of an approximately spherical half shell which is supported with its edge on said handle branch and in its central part is connected to said bearing shaft.

5. Instrument as defined in claim 4, wherein said bearing shaft includes a stepped metal sleeve in which a shaft connected to said head is inserted.

6. Instrument as defined in claim 5, wherein from the opposite side of said shaft a counterpart which is connected to said shaft and covers the end face of said metal sleeve is inserted into the latter.

7. Instrument as defined in claim 6, wherein the connection between shaft and counterpart is a detent connection.

8. Instrument as defined in claim 1, characterized in that said moved working part has a spherical end which is connected to said working part via a web of smaller dimensions.

9. Instrument as defined in claim 8, wherein said driver (12) is a blind hole bore in said handle branch (2) which extends essentially parallel to said slot-shaped opening (25) and is open via a lateral longitudinal slot (13), the width of which is smaller than the diameter of said spherical end (10) and larger than the width of said web (11).

10. Instrument as defined in claim 1, characterized in that said slot is arranged essentially perpendicular to the direction of displacement of said working part.

\* \* \* \* \*